(12) United States Patent
Lucas et al.

(10) Patent No.: US 6,322,592 B2
(45) Date of Patent: *Nov. 27, 2001

(54) MACRO-POROUS COMPOSITE SUPPORT FOR MEDICINAL SUBSTANCE(S) THAT CAN BE USED AS A BONE RECONSTITUTION MATERIAL AND A METHOD OF PRODUCING IT

(75) Inventors: Anita Lucas; Jean-Francois Michel, both of Rennes; Jean-Francois Gaude, Acigne; Claude Carel, Rennes, all of (FR)

(73) Assignee: Universite de Rennes, Rennes (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,375

(22) PCT Filed: Jan. 2, 1997

(86) PCT No.: PCT/FR97/00007

§ 371 Date: Sep. 28, 1998

§ 102(e) Date: Sep. 28, 1998

(87) PCT Pub. No.: WO97/26024

PCT Pub. Date: Jul. 24, 1997

(30) Foreign Application Priority Data

Jan. 15, 1996 (FR) .................................................. 96 00560

(51) Int. Cl.$^7$ ....................................................... A61F 2/36
(52) U.S. Cl. ..................................... 623/23.51; 623/23.61
(58) Field of Search ............................ 623/11, 16, 23.61, 623/23.62, 23.63, 23.51; 604/265; 501/124; 424/488

(56) References Cited

U.S. PATENT DOCUMENTS

| 3,890,107 | | 6/1975 | White et al. . | |
|---|---|---|---|---|
| 5,007,930 | * | 4/1991 | Dorman et al. | 623/16 |
| 5,252,525 | * | 10/1993 | Gonzales et al. | 501/124 |
| 5,433,751 | * | 7/1995 | Christel et al. | 623/16 |
| 5,585,114 | * | 12/1996 | Besemer et al. | 424/488 |
| 5,741,329 | * | 4/1998 | Agrawal et al. | 623/11 |
| 5,902,283 | * | 5/1999 | Darouiche et al. | 604/265 |

FOREIGN PATENT DOCUMENTS

| 0 022 724 | 9/1981 | (EP) . |
|---|---|---|
| 0 159 087 | 10/1985 | (EP) . |
| 0 395 187 | 10/1990 | (EP) . |
| 2 637 502 | 4/1990 | (FR) . |
| WO 87/07826 | 12/1987 | (WO) . |
| WO 94/26322 | 11/1994 | (WO) . |

* cited by examiner

Primary Examiner—Corrine McDermott
Assistant Examiner—Hieu Phan
(74) Attorney, Agent, or Firm—Merchant & Gould PC

(57) ABSTRACT

The invention relates to a macro-porous composite that can be used as a bone reconstitution material. The composite is made up of a combination of synthetic aragonite and at least one medicinal substance such as notably, an antibiotic. The invention also relates to a method of producing a composite which includes producing a mixture includes grains of synthetic aragonite and at least one porogenic agent, compacting the mixture and heating the product obtained in such a way as to eliminate the porogenic agent. At least one medicinal substance is included before or after the step of eliminating of the porogenic agent.

11 Claims, 2 Drawing Sheets

MACRO-POROUS COMPOSITE SUPPORT FOR MEDICINAL SUBSTANCE(S) THAT CAN BE USED AS A BONE RECONSTITUTION MATERIAL AND A METHOD OF PRODUCING IT

FIELD

The invention relates to the field of bio-materials that can be used to replace a part of the bone system.

The bio-materials are materials used to replace a part of the living system or to function with it. They are made up of materials that are foreign to the receiver, implanted in him in order to restore the morphology and/or the function of tissues damaged by trauma or by a disease. Therefore they all have the novelty of having to work under biological constraints.

The bio-material must satisfy physico-chemical characteristics appropriate to the site where it will be implanted and to the function that it will have to fulfil. The chances of success of a bio-material in an organism result from the product of many factors which will all have to be controlled.

From the point of view of implants carried out with such bio-materials, the bio-compatibility of them is defined as the control of reactions of the organism with respect to them during the entire duration of contact between the bio-material being considered and the organism. Mechanical and biological properties of such a product are therefore very closely linked.

The invention relates more precisely to bio-materials that can be used as bone reconstitution materials.

BACKGROUND

In this field, coral has been proposed and has been widely used for ten years or so. This natural material has a mineral exoskeleton of open porosity formed, in the main, of aragonite. Aragonite is an allotropic form of calcium carbonate, which crystallises in an orthorhombic system with lattice parameters a=4.9623 (3)Å, b=7.968 (1)Å, c=5.7439 Å for Z=4. Its theoretical density is d=2.93.

Within the state of the technology, it has been proposed to use preparations based on coral as bone reconstitution materials within the field of paradontology (paradontal diseases, bone surgery correcting loss of substance). This material is used in this context in the form of granules of size ranging from 300 to 450 gm for the filling in of paradontal defects and from 600 to 1000 pm for the filling of sockets after dental extractions. Granules are preferred to blocks which lead to the exfoliation of the coral fragment after its implantation, the size of the particles recommended for the filling in of paradontal defects then being from 300 to 500 pm.

French patent application FR 2637502 describes a bone reconstitution material made up of madreporous coral washed of any original organic substances and containing an organic osteogenesis accelerator in the form of a proteinic gel based on Type I collagen.

International patent application WO 94/26322 discloses a porous material made up of a coral skeleton (of the Porites, Acropora, Goniopora, Lobophyllia, Simphyllia or Millipora type) and a growth factor capable of being an osteo-inductive agent.

European patent application EP 395187 describes a bio-material made up of coral coated with a layer of hydroxyapatite.

Experience has shown that coral has a high bio-compatibility that confirms that it is of interest as a material for bone reconstitution.

However, such a material has the major disadvantage of high cost brought about by its processing when it is to be used as an implant material. In practice, coral gathered from nature must be divided up, then washed and incubated for several days in products such as sodium hypochlorite in order to remove all organic substances from it. Such an incubation must be carried out in such a way that the product used is able to penetrate into the entire structure of the porous coral. Blocks of coral treated in this way must then be broken up and sorted into granule size ranges, or machined in order to be made geometrically suitable for the implantation sites and then washed once again.

Furthermore, coral has a porosity that it is not possible to control. In relation to the desired speed of resorption, it is advisable to choose this or that type of coral in relation to its natural porosity.

SUMMARY

The main objective of this invention is to provide a bio-material that can be used as a bone reconstitution material and which permits this problem to be resolved.

Another objective of the invention is to disclose such a material that can be produced in such a way that its properties, notably its porosity properties, can be modulated as a function of the use to which it is to be put.

Yet another objective is to provide such a material that is able to include one or more medicinal substances with a view to administering these substances with their release being to varying extents.

These various objectives as well as others which will become apparent in what follows have been achieved thanks to the invention which relates to a macro-porous composite that can be used as a bone reconstitution material, characterised in that it is made up of a combination of synthetic aragonite and at least one medicinal substance.

Such a composite has numerous advantages.

In the first place, it is a material based on aragonite and it can be resorbed slowly in situ. The medicinal substance that it includes will be able to be progressively released into the organism and there can be a delay effect.

The fact that at least one medicinal substance is included in the synthetic aragonite substrate offers additional interesting potential therapeutic features through the local action of this medicinal substance at a high concentration.

Furthermore and above all, since the aragonite used is synthetic, it will be possible to modulate certain parameters at the time it is synthesised. Hence it will be possible to provide an aragonite substrate having pores of smaller or greater size, having open or closed porosity, or a substrate that allows the production of a material that is more or less dense or more or less rigid. Furthermore one may modulate the nominal concentration of the medicinal substance or substances in the composite. The use of synthetic aragonite therefore offers a considerable advantage compared with natural substrates, the pores of which obviously cannot be varied in size or nature depending on the objective sought and into which one cannot simply introduce foreign substances in specific quantity.

Finally, it should be noted that the cost price of such a composite will be much less than that of preparations based on coral from the state of the technology. More precisely, one may estimate that the cost price would be about 10 times less than that for preparations based on coral.

The composite according to the invention will notably be used in odontology, in particular in buccal surgery and in paradontology and in surgical orthopaedics. However it should be noted that the field of application of such composites is not limited to this one domain of dentistry and that later extension to bone surgery in general is totally conceivable.

Preferably, the synthetic aragonite will represent between about 85% and 99.5% of the total mass of the said composite. However depending on the use that will be made of the composite produced, one may consider in certain cases going outside of such a range.

According to a particularly interesting variant, said medicinal substance is an antibiotic. The significance of antibiotics is known and, as mentioned above, the composite according to the invention allows the medicinal substance included in the composite to be administered with a retard effect. This is particularly of interest for antibiotics. Furthermore, one may consider that such an antibiotic associated with an aragonite substrate in this way could have a local action at high concentration, with a quantity 100 to 1000 times less than that required when administered through the normal route.

Advantageously said antibiotic is a broad spectrum antibiotic such as metronidazole, the action of which on anaerobic germs is much sought after in bone surgery.

The invention also relates to a method of manufacturing such a macro-porous composite characterised in that it consists of producing a mixture that includes grains of synthetic aragonite and at least one porogenic agent, compacting said mixture and heating the product obtained in such a way that said porogenic agent is eliminated, at least one medicinal substance being included before or after said step of eliminating said porogenic agent.

The medicinal substance or substances, if one or more powders, can be added before heating, or if one or more fluid substances after heating, by impregnation or by aspiration.

Preferably, said porogenic agent is a solid compound also being in powder form. The size of the grains of powder making up said porogenic agent will approximately correspond to the size of the pore of the composite. According to an interesting variant, the size of these grains will preferably be between 100 and 1000 μm.

Also preferably, said porogenic agent is naphthalene ($C_{10}H_8$). As will be explained in greater detail below, it has been observed that the presence of naphthalene during the compacting stage confers a multi-directional character onto the orientation of the grains of aragonite that allows one to avoid transverse breakage of the tablets obtained using the method according to the invention. One could also consider using other types of porogenic agents known from the state of the art.

In the preferred case where the porogenic agent used is naphthalene, said heating step implemented in the context of the method according to the invention is advantageously carried out at a temperature of around 110° C. leading to the sublimation of the naphthalene. It will be understood that in the case where a porogenic agent other than naphthalene is chosen, another heating temperature may be used.

In a general manner, when said medicinal substance is introduced before said step of elimination of the porogenic agent, said heating step will advantageously be carried out at temperatures of the order of 110° C.

However, when according to a variant of the invention, said medicinal substance is introduced after said step of eliminating said porogenic agent, said heating step may be carried out at temperatures of the order of 400° C. or more.

Also preferentially, said compacting step is carried out by uniaxial pressing. Such a pressing has the advantage of being able to be easily implemented. One might be afraid that this type of pressing would lead to preferential orientation of the crystals of aragonite. However it turns out that the presence in the mixture of grains of naphthalene and the sublimation of this porogenic agent leads to the advantageous provision of crystals that are relatively disoriented.

It is possible to consider the production of the aragonite substrate via several synthesis routes known from the state of the technology. Aragonite, under ambient conditions of temperature and pressure is not the thermodynamically stable form of calcium carbonate which makes obtaining it more difficult than obtaining calcite which is the stable form.

One of the possible routes of access is to reproduce in the laboratory the conditions of precipitation in an aqueous phase that are present in 30 nature, under ordinary temperatures and pressures.

Aragonite can thus be obtained from sea water, natural or artificial, with a high concentration of $Ca^{2+}$ ions.

Precipitation can then occur after generation of carbonate ions from a solution saturated with hydrogencarbonate, by removal of $CO_2$.

Another route consists of adding carbonate ions to the solution of $Ca^{2+}$ ions in the form of a soluble carbonate such as $Na_2CO_3$. In this case, the addition of ions that favour the precipitation of aragonite is essential.

The major disadvantage of these methods is slow kinetics.

The carbonation of lime water, possibly containing additives, or of a solution of calcium nitrate, in a basic environment also permits aragonite to be obtained under certain conditions.

Other methods are also known but they lead to low quantities of aragonite and/or the presence of other forms (calcite, vaterite).

The invention also relates to a method of synthesising synthetic aragonite, that permits the provision of aragonite possibly containing another form as an impurity, notably calcite, under conditions that are economically interesting. Such a method is characterised in that it consists of bringing potassium hydrogencarbonate into contact with calcium chloride at the rate of 2 moles of potassium hydrogencarbonate to one mole of calcium chloride, in a solution at boiling point and at a pH of between 7 and 9.

BRIEF DESCRIPTION OF THE DRAWINGS

The invention will be more easily understood, with the help of the description that will follow of a non-limitative embodiment of the invention, making reference to the drawings in which.

DETAILED DESCRIPTION

Synthesis of the Aragonite

A solution of 0.1 M calcium chloride was continuously added to a 0.1M solution of potassium hydrogencarbonate having a pH of 8.6 at 20° C., at the rate of 2 moles of potassium hydrogencarbonate for 1 mole of calcium chloride. The addition was carried out at temperature (between 90° C. and 100° C.) with the help of a controlled addition device. The solution was placed on a hot plate with a magnetic stirrer, the agitation being provided by a magnetised bar turning at a speed of 500 rpm.

This addition lead to precipitation of calcium carbonate in its aragonite form, in accordance with the reaction that can be written as:

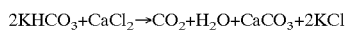

$$2KHCO_3 + CaCl_2 \rightarrow CO_2 + H_2O + CaCO_3 + 2KCl$$

The precipitate obtained was filtered onto paper using a Buchner funnel preheated to the drying temperature. Then the precipitate was washed with boiling de-ionised water (≈100° C.) and then dried in an oven held at 110±2° C.

Using X-ray diffraction, it was verified that such a synthesis method allows one to obtain calcium carbonate $CaCO_3$ in the form of aragonite with the absence of other phases.

Figure 1:
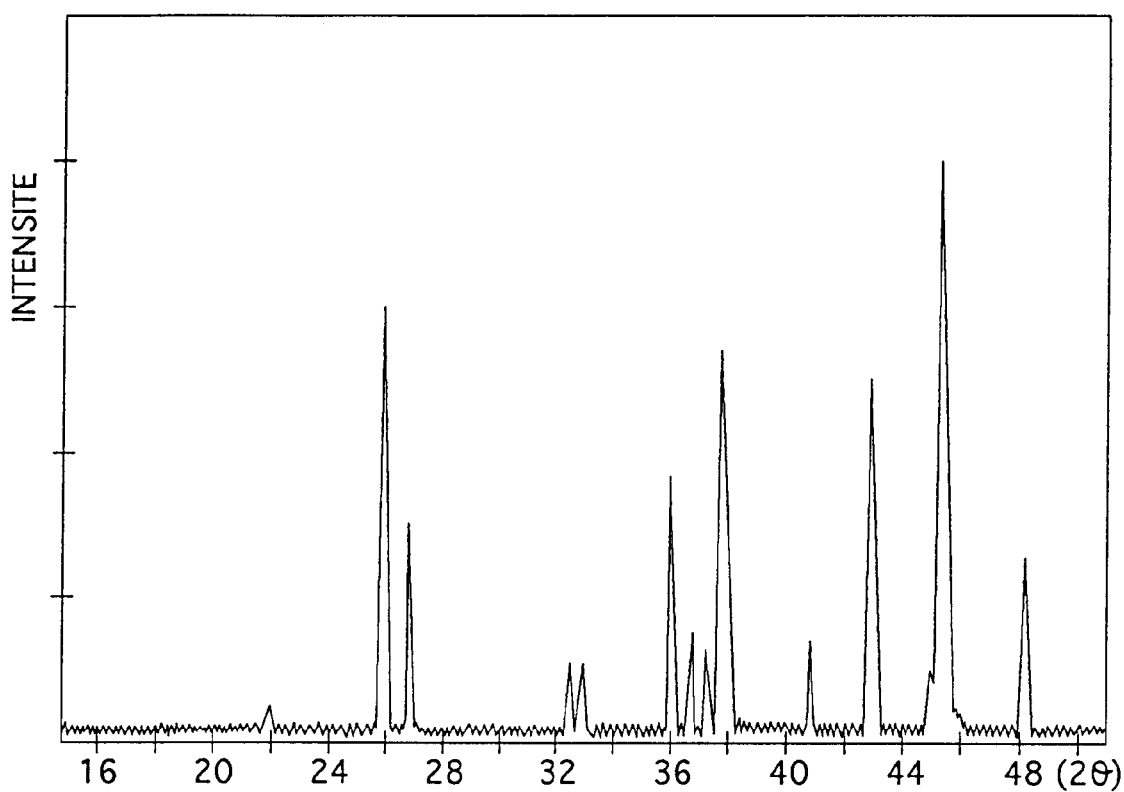
FIG. 1 represents the X-ray diffraction diagram of the aragonite obtained by synthesis in the context of this embodiment example.

More precisely, the X-ray diffraction diagram was recorded at ambient temperature and pressure. This diagram is represented in FIG. 1.

The granulometric analysis by volume of the product obtained showed that all the grains had an equivalent diameter less than 62 μm. The number distribution indicated that 99.8% of the particles had an equivalent diameter less than 1.8 μm.

Preparation of the Composite

Naphthalene with a purity greater than 99% (Scintillation grade from the company Aldrich) was ground manually in a mortar and sieved using a vertical vibration sieving machine for 15 minutes. The openings in the sieves in the sieving machine were successively 250, 160 and then 100 μm.

A specific fraction of naphthalene was recovered from the sieve with the 100 μm openings. Abstracting from the natural tendency for particles of naphthalene to agglomerate, it could be verified that the diameter of the particles recovered lay between 100 and 160 μm.

In addition, metronidazole (1-(2-hydroxy-ethyl)-2-methyl-5-imidazole) in the form of a 99.95% pure, very pale yellow crystalline powder, supplied by the company Spécia (Rhône Poulenc Group Rorer Spécia) was ground by hand and sieved using a vertical vibration sieve machine for 15 minutes. The sieve openings used in the sieving machine were 160 and 100 pm.

The sieved metronidazole was then manually mixed, without grinding with the aragonite powder obtained according to the method described above and then with the particles of ground naphthalene.

Three different mixes were produced, in which the ground metronidazole was always 5% of the total mass of the said mixture, the naphthalene being successively 28.6%, 21.1% and 14.6% of this total mass.

Figure 2:
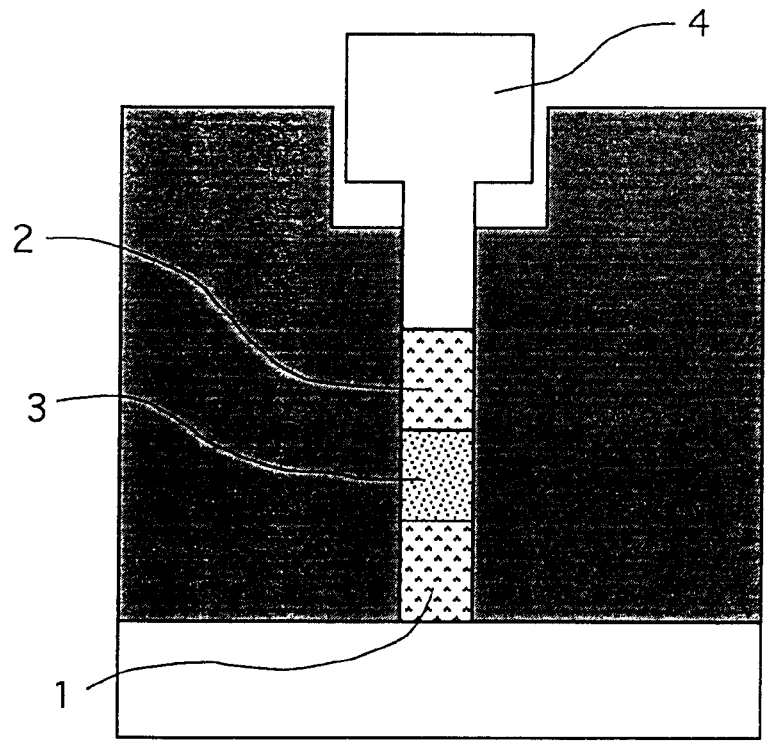
FIG. 2 represents a diagrammatic view of a tabletting mould used for the compacting of a aragonite-metronidazole-naphthalene mixture

A mass of 0.1 g of each of the mixtures of synthetic aragonite, metronidazole and naphthalene produced was then placed between the two metal cylinders 1,2 of a tabletting mould (SPECAC—registered trademark—diameter 6 mm) as is represented in diagrammatic form in FIG. 2. The compacting of the mixtures 3 was carried out by application of a strong uniaxial pressure of 900 MPa (9 kbar) using a piston 4. This pressure was maintained for 5 minutes and was then progressively reduced down to atmospheric pressure.

The naphthalene was eliminated by heating the tablets in an oven fitted with an electronic regulator at 90° C., under a primary vacuum, for six hours. Following this treatment, the tablets were treated at 110° C., under atmospheric pressure for 16 to 17 hours, and then cooled in a dry atmosphere in a desiccator.

A variant of the preparation of the tablets, after having eliminated the porogene from the porogene/aragonite mixture at the usual temperatures, consists of bringing the porous aragonite thus obtained to temperatures of the order of 400° C. or more, possibly under carbon dioxide $CO_2$ in order to cause sintering that allows the strength of the tablet to be increased. After cooling this can then be charged with medicinal substance(s) by impregnation or aspiration.

Properties of the Tablets Obtained

The products obtained following the operation described above are in the form of tablets free of naphthalene with a thickness varying from 1.92 mm to 2.04 mm for a diameter of 6 mm.

The table below indicates the geometric density and the porosity of the three tablets corresponding to the mixtures above.

| % (mass) naphthalene | Geometric density | Porosity (%) |
| --- | --- | --- |
| 28.6 | 1.28 ± 0.02 | 54.0 ± 1.3 |
| 21.1 | 1.47 ± 0.03 | 47.1 ± 1.6 |
| 14.6 | 1.64 ± 0.03 | 41.0 ± 1.6 |

Figure 3:
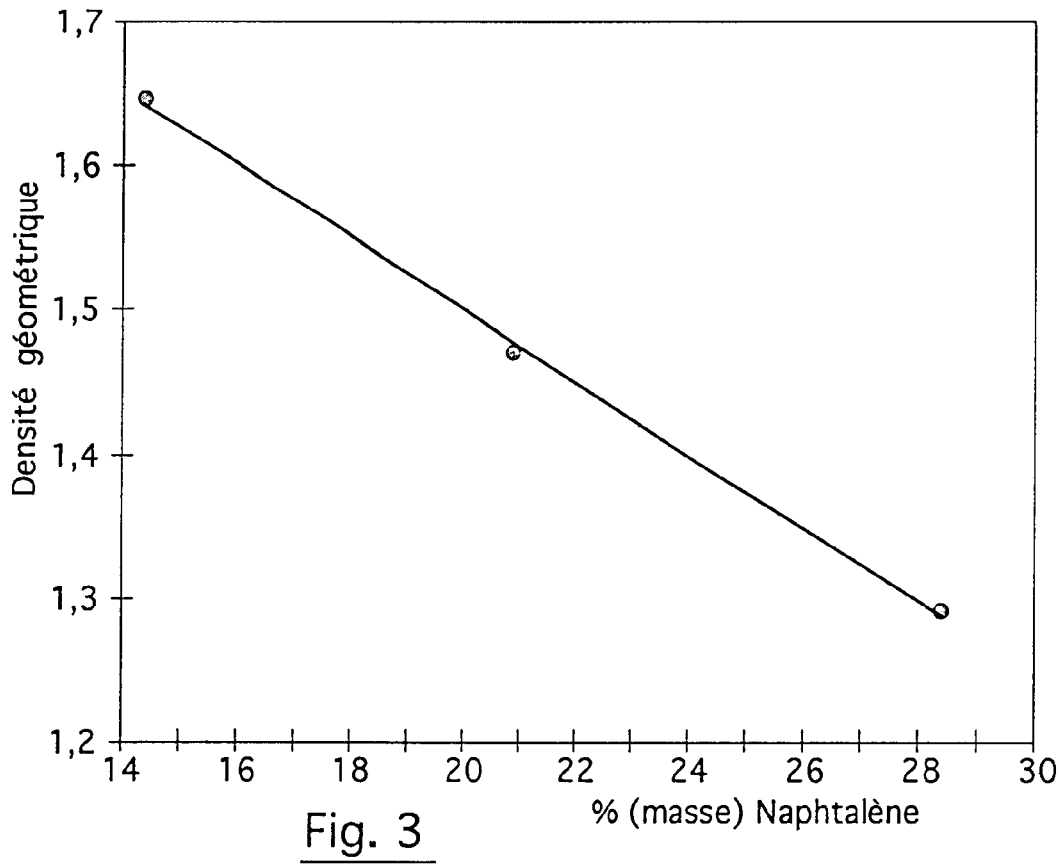
FIG. 3 represents the change in the geometric density of the composites obtained as a function of the percentage by mass of naphthalene used.
Figure 4:
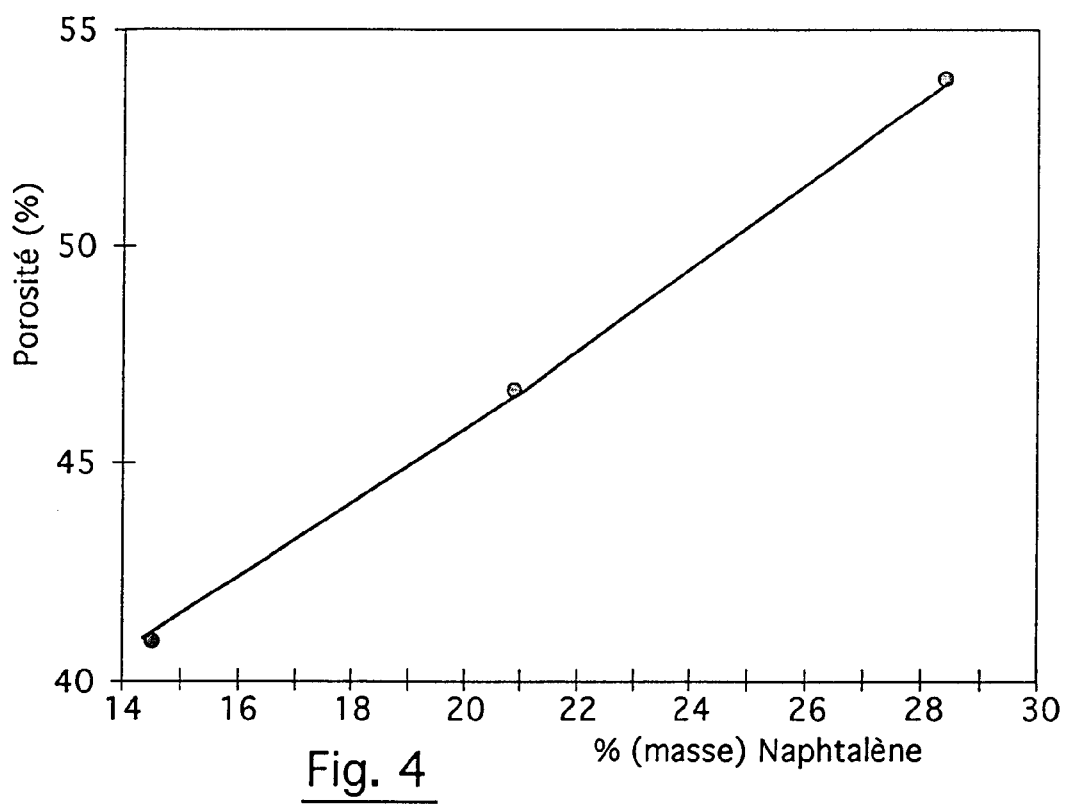
FIG. 4 represents the change in the porosity of the composites obtained as a function of the percentage by mass of naphthalene used

As one can see in FIGS. 3 and 4 showing the data from the table above, the geometric density of the composite obtained decreases approximately linearly when the content of the porogenic agent used increases and, conversely, the porosity of the composite increases approximately linearly when the content of the porogenic agent used increases.

Observation of samples under the electron microscope shows the nature of the tablets and the keying of the metronidazole crystals into the porous inorganic matrix at well differentiated sites. The metronidazole crystals are either encapsulated or positioned along a continuous line of porosity.

The use of naphthalene as the porogenic material lead to egg-shaped macro-pores being provided the size of which is related to the choice made for the size of naphthalene particles, being between about 100 and about 160 μm. Furthermore, it has already been indicated that the presence of naphthalene during compacting confers a multidirectional character on the orientation of the aragonite particles that allows one to avoid transverse fracture of the tablets.

The embodiment of the invention that has been described here does not have the purpose of reducing the range of the invention. Hence it is possible to consider the introduction of modifications without departing from the scope of the invention as defined in the appended claims. Notably, the use of a medicinal substance other than an antibiotic such as metronidazole might be considered, from the point where this substance may be incorporated before or after the manufacture of said porous composite. Of course a porogenic agent other than naphthalene could be considered although this still remains the preferred porogenic agent.

What is claimed is:

1. A bone reconstitution composite consisting of a synthetic aragonite substrate having pores and at least one medicinal substance, wherein the synthetic aragonite represents between 85% and 99.5% of the total mass of the composite.

2. The bone reconstitution composite according to claim 1, wherein said medicinal substance is an antibiotic.

3. The bone reconstitution composite according to claim 2, wherein said antibiotic is metronidazole.

4. A method of producing a bone reconstitution composite consisting of a synthetic aragonite substrate having pores and at least one medicinal substance, wherein the method comprises of producing a mixture comprising grains of synthetic aragonite and at least one porogenic agent, compacting said mixture and heating the product obtained in a way that said porogenic agent is eliminated, and including the additional step of adding the at least one medicinal substrate before or after the step of eliminating said porogenic agent.

5. The method according to claim 4, wherein said porogenic agent is a solid compound in the form of a powder.

6. The method according to claim 5, wherein said powder is made up of particles having a mean diameter ranging from 100 μm to 1000 μm.

7. The method according to claim 5, wherein said porogenic agent is naphthalene.

8. The method according to claim 4, wherein said heating step is carried out at temperatures on the order of 110° C. when said medicinal substance is introduced before said step of eliminating said porogenic agent.

9. The method according to claim 4, wherein said heating step is carried out at temperatures on the order of 400° C. or more when said medicinal substance is introduced after said step of eliminating said porogenic agent.

10. The method according to claim 4, wherein said compacting step is carried out by uniaxial pressing at 900 MPa.

11. A method of synthesising synthetic aragonite wherein the method consists of bringing potassium hydrogencarbonate into contact with calcium chloride at the rate of 2 moles of potassium hydrogencarbonate to one mole of calcium chloride at boiling point and at a pH of between 7 and 9.

* * * * *